US00PP19428P2

(12) United States Plant Patent
Heims

(10) Patent No.: US PP19,428 P2
(45) Date of Patent: Nov. 4, 2008

(54) ***ECHINACEA* PLANT NAMED 'PINK POODLE'**

(50) Latin Name: *Echinacea purpurea*
Varietal Denomination: Pink Poodle

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/986,116

(22) Filed: Nov. 19, 2007

(51) Int. Cl.
*A01H 5/00* (2006.01)

(52) U.S. Cl. ..... Plt./428
(58) Field of Classification Search ..... Plt./428
See application file for complete search history.

*Primary Examiner*—Annette H Para
*Assistant Examiner*—S. B. McCormick-Ewoldt
(74) *Attorney, Agent, or Firm*—Klarquist Sparkman, LLP

(57) ABSTRACT

A new and distinct *Echinacea* plant named 'Pink Poodle' characterized by large, double, bright pink inflorescences, well-branched flower stalks, strong flowering stems, and excellent vigor.

1 Drawing Sheet

Botanical denomination: *Echinacea purpurea.*
Variety designation: 'Pink Poodle'.

BACKGROUND OF THE INVENTION:

The present invention relates to a new and distinct cultivar of *Echinacea* and given the cultivar name 'Pink Poodle'. *Echinacea* is in the family Asteraceae. This new cultivar was found as a seedling out of a sowing of *Echinacea purpurea* 'Doubledecker' (unpatented).

Compared to *Echinacea* 'Doubledecker' the new variety has many more disc florets that have been converted to ray florets.

This new *Echinacea* cultivar is distinguished by:

1. large, double, bright pink inflorescences
2. well-branched flower stalks
3. strong flowering stems
4. excellent vigor This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a close up of one inflorescence of *Echinacea* 'Pink Poodle' from a plant growing in the ground in full sun in the field in late summer in Canby, Oreg.

FIG. 2 shows the whole plant.

DETAILED PLANT DESCRIPTION

The following is a detailed description of the new *Echinacea* cultivar based on observations of a 9-month-old specimen growing in the ground in the field in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—45 cm wide and 81 cm tall to top of flowers.
- *Form.*—Basal clump.
- *Vigor.*—Excellent.
- *Roots.*—Fibrous, with many downward growing and few laterals, ivory in color (Yellow White 158D), roots develop easily from cuttings from the crown.

Stem (flowering):
- *Type.*—Ascending, branching 3 to 9 times per stem.
- *Size.*—59 cm tall to the last leaf of the main stem and 14 mm wide at base.
- *Internode length.*—5 cm to 8 cm.
- *Surface texture.*—Strigose.
- *Color.*—Yellow Green 146A mottled with Yellow Green 146D.

Leaf (basal):
- *Type.*—Simple.
- *Shape.*—Ovate.
- *Arrangement.*—Basal.
- *Blade size.*—Grows to 22 cm long and 9.5 cm wide.
- *Margins.*—Entire shallowly broadly serrate.
- *Apex.*—Acuminate.
- *Base.*—Attenuate, continuing down petiole.
- *Surface texture.*—Strigose on both sides.
- *Venation.*—Pinnate.
- *Color.*—Topside, Yellow Green 147A and bottom side closest to Yellow Green 147B with the vein Yellow Green 147D.
- *Petiole description.*—Clasping, grows to 16 cm long and 18 mm wide where clasping, strigose, Yellow Green 147D with bottom half tinted Greyed Purple 187C to 187D.

Leaf (stem):

*Type.*—Simple.

*Shape.*—Lanceolate to ovate.

*Arrangement.*—Alternate.

*Blade size.*—Grows to 19 cm long and 7.4 cm wide.

*Margins.*—Coarsely serrate to entire.

*Apex.*—Acute.

*Base.*—Attenuate, continuing down petiole.

*Surface texture.*—Strigose on both sides.

*Venation.*—Pinnate.

*Color.*—Topside, Yellow Green 147A and bottom side closest to Yellow Green 147B with the vein Yellow Green 147D.

*Petiole description.*—Clasping, grows from 7 cm long to sessile and 10 mm wide where clasping, strigose, Yellow Green 147B.

Inflorescence:

*Type.*—Composite on terminal stalked heads.

*Number of flowering stems per plant in summer.*—1 to 3.

*Flowering stem.*—Grows to 72 cm tall from the base of the plant to the terminal inflorescence and can grow to 14 cm long from the top leaf of the base of a flower head; branching 3 to 9 times per stem, from 3 to 13 flowers per stem; diameter growing to 12 mm wide near the inflorescence; strigose, Yellow Green 146A mottled with Yellow Green 146D.

*Size.*—Grows to 11 cm wide and 7 cm deep.

*Form.*—Double, ray florets grow from receptacle instead of disc florets.

*Immature inflorescence.*—2.5 cm wide and 2.5 cm deep, ray florets held at a 45 degree angle and rolled up so only the back color shows, Yellow Green 160B, Yellow Green 147A.

*Ray florets.*—Occurring as normal around edge of disc as well as sporadically in the disc area; without stamen, most without pistil; about 270 full size and 90 under size; oblanceolate with the tip two toothed (each acute), entire margins, base attenuate, grows to 55 mm long and 10 mm wide, glabrous on both sides; topside color closet to Red Purple 67A, bottom side closest to Red Purple 66D; infertile ovary 4 mm long, White 155A.

*Disc florets.*—Tubular; in three types each with one persistent stiff bract (15 mm long and Greyed Purple 187A on tip to Orange 31A to Yellow Green 144A bottom half); 2 types with corolla enlarged and Red Purple 67A (narrow sterile type about 34 in number and fertile fat type about 40 in number), 1 type normal sized and fertile with corolla Greyed Purple 185A (about 152 in number); each about 10 mm long and 2.5 mm wide, corolla 7 mm long and 1.5 mm wide, 5 lobed, glabrous; pistil 10 mm long, ovary 3.5 mm long, White 155A, style 6 mm long Yellow Green 145D, with 2-branched stigma spreading 2 mm wide, Black 202A; stamen 4 in number, 3.5 mm long, anthers 2.5 mm long and Black 202B, filaments 1 mm long, Yellow White 158D, pollen sparse, Yellow Orange 17A.

*Phyllaries.*—In 4 leafy series, area 3.7 cm wide and 10 mm deep, lobes lanceolate in shape, reflexed, grow to 12 mm long and 5 mm wide, Yellow Green 147B, margins entire, strigose, tip acute.

*Receptacle.*—Grows to 19 mm wide and 20 mm deep, White 155D.

*Bloom period.*—July through October in Canby, Oreg.

*Fragrance.*—Slight.

*Lastingness.*—Each inflorescence lasts about two weeks in Canby, Oreg.

Seeds: Average number of 7 seeds/head, each 5 mm long and 2.5 mm wide, oval, Brown 200C.

*Fertility.*—Good.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

* * * * *

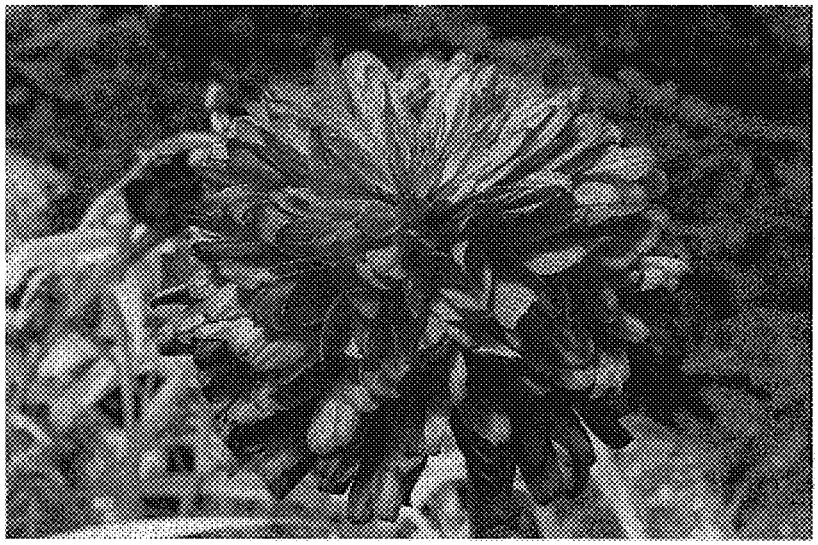
Figure 1 above, figure 2 below.
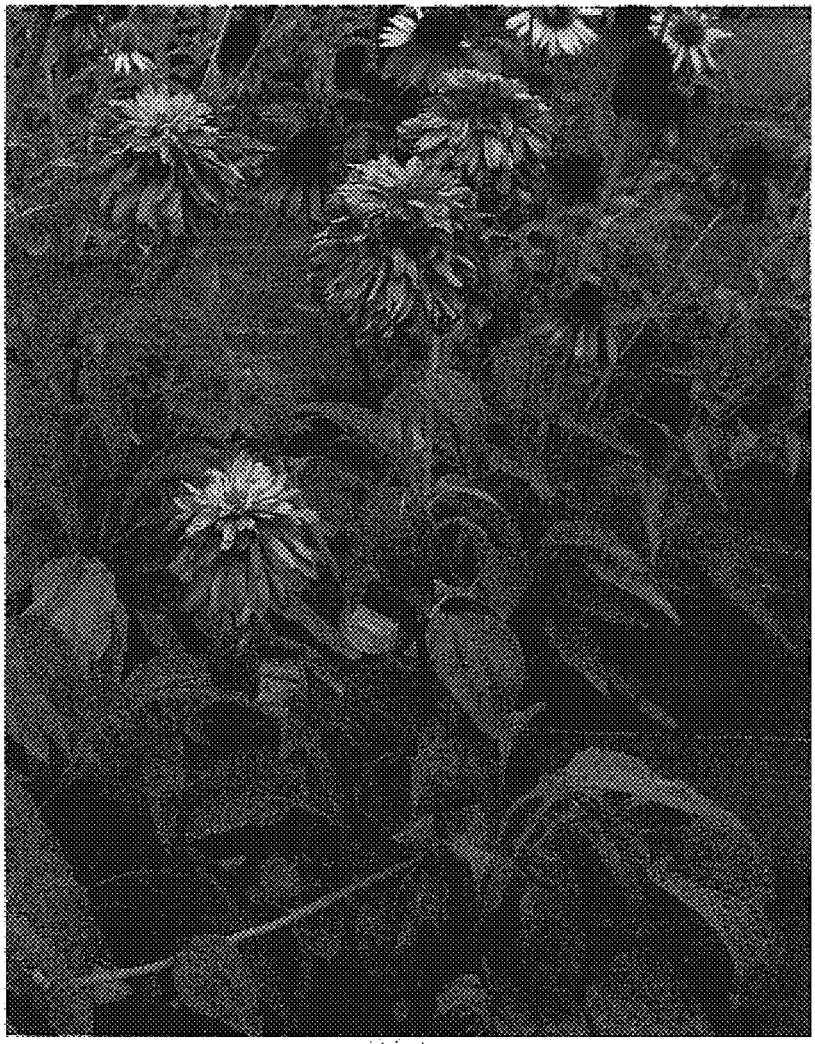

UNITED STATES PATENT AND TRADEMARK OFFICE

CERTIFICATE OF CORRECTION

PATENT NO. : PP 19,428 P2
APPLICATION NO. : 11/986116
DATED : November 4, 2008
INVENTOR(S) : Daniel M. Heims It is certified that error appears in the above-identified patent and that said Letters Patent is hereby corrected as shown below:

Column 2, line 31, “Entire shallowly” should be --Entire to shallowly--.

Column 3, line 23, “of the base” should be --to the base--.

Signed and Sealed this

Fourteenth Day of April, 2009

John Doll

JOHN DOLL
*Acting Director of the United States Patent and Trademark Office*